(12) United States Patent
Harmer et al.

(10) Patent No.: US 7,625,941 B2
(45) Date of Patent: *Dec. 1, 2009

(54) IONIC LIQUIDS

(75) Inventors: Mark Andrew Harmer, Kennett Square, PA (US); Christopher P. Junk, Wilmington, DE (US); Leo Ernest Manzer, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 418 days.

This patent is subject to a terminal disclaimer.

(21) Appl. No.: 11/525,751

(22) Filed: Sep. 22, 2006

(65) Prior Publication Data

US 2007/0066834 A1  Mar. 22, 2007

Related U.S. Application Data

(60) Provisional application No. 60/719,459, filed on Sep. 22, 2005.

(51) Int. Cl.
*A61K 31/4015* (2006.01)
*C07D 207/12* (2006.01)

(52) U.S. Cl. .............. 514/424; 548/541; 548/543; 252/364

(58) Field of Classification Search ............. 548/541, 548/543; 514/424; 252/364
See application file for complete search history.

(56) References Cited

U.S. PATENT DOCUMENTS

| 5,608,105 | A | 3/1997 | Fitzpatrick | |
|---|---|---|---|---|
| 5,859,263 | A | 1/1999 | Ghorpade et al. | |
| 6,054,611 | A | 4/2000 | Farone et al. | |
| 6,720,459 | B2 | 4/2004 | Sunkara et al. | |
| 6,818,593 | B2 | 11/2004 | Manzer | |
| 7,157,588 | B2 * | 1/2007 | Harmer et al. | 548/543 |
| 7,314,962 | B2 * | 1/2008 | Harmer et al. | 585/422 |
| 7,402,711 | B2 * | 7/2008 | Harmer et al. | 568/617 |
| 7,405,330 | B2 * | 7/2008 | Harmer et al. | 568/619 |
| 2003/0233011 | A1 | 12/2003 | Fagan et al. | |

FOREIGN PATENT DOCUMENTS

WO   WO 03/048078 A2   6/2003

OTHER PUBLICATIONS

Rogers et al., "Ionic Liquids—Solvents of the Future?", Science (2003) 302:792-793.
Merrigan et al., "New fluorous ionic liquids function as surfactants in conventional room-temperature ionic liquids", Chem. Comm. (2000) 2051-2052.
Wasserscheid et al., "Hydrogensulfate and tetrakis(hydrogensulfato)borate ionic liquids: synthesis and catalytic application in highly Bronsted-acidic systems for Friedel-Crafts alkylation", Green Chemistry (2002) 4:134-138.
Wasserscheid & Keim, "Ionic Liquids—New 'Solutions' for Transition Metal Catalysis", Angew. Chem. Int. Ed. (2000) 39:3772-3789.
Sheldon et al., "Catalytic reactions in ionic liquids", Chem. Comm. (2001) 2399-2407.

* cited by examiner

*Primary Examiner*—Golam M Shameem

(57) ABSTRACT

The present invention relates to compositions of matter that are useful as ionic liquids. The compositions of the invention are based on an N-substituted pyrrolidinone, said pyrrolidinone having a pendant ammonium cation that is separated from the pyrrolidone ring by a variable length alkyl spacer. The compositions comprise fluoroalkyl sulfonate anions.

4 Claims, No Drawings

IONIC LIQUIDS

CROSS-REFERENCE TO RELATED APPLICATION

This application claims priority under 35 U.S.C. §119 from U.S. Provisional Application Ser. No. 60/719,459, filed Sep. 22, 2005.

FIELD OF THE INVENTION

This invention relates to compositions of matter that are useful as ionic liquids.

BACKGROUND

Ionic liquids are liquids composed of ions that are fluid around or below 100 degrees C. (Science (2003) 302:792-793). Ionic liquids exhibit negligible vapor pressure, and with increasing regulatory pressure to limit the use of traditional industrial solvents due to environmental considerations such as volatile emissions and aquifer and drinking water contamination, much research has been devoted to designing ionic liquids that could function as replacements for conventional solvents.

The present invention provides novel compositions comprising fluorinated anions that are useful as ionic liquids. Fluorous ionic liquids have been described. For example, Merrigan, et al. (Chem. Comm. (2002) 2051-2052) describe imidazole-derived ionic liquids having fluorous tails, and Wasserscheid, et al. (Green Chemistry (2002) 4:134-138) describe the synthesis of imidazolium-derived ionic liquids having a bis(trifluoromethanesulfonato)amide anion. In addition, Rudyuk, et al. describe the synthesis of N-polyfluoroethyl and N-2-chlorodifluorovinyl derivatives of azoles, such as imidazole, pyrazole and triazole.

The compositions of the present invention are fluoroalkyl sulfonate-based compositions comprising a pyrrolidinone-derived cation that may exhibit unique properties due to separation of the ammonium cation from the pyrrolidinone ring using a variable-length alkyl spacer group.

SUMMARY

In its broadest aspect, the present invention relates to a composition of matter comprising an ammonium cation and an anion of the Formula:

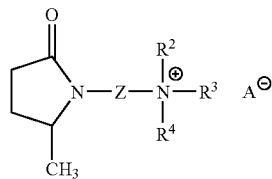

wherein:
(i) Z is —$(CH_2)_n$—, wherein n is an integer from 2 to 12;
(ii) $R^2$, $R^3$ and $R^4$ taken independently are H, —$CH_3$, —$CH_2CH_3$ or $C_3$ to $C_6$ straight-chain or branched monovalent alkyl; and
(iii) $A^-$ is $R^5$—$SO_3^-$ or $(R^6$—$SO_2)_2N^-$; wherein $R^5$ and $R^6$ are independently selected from the group consisting of:
(a) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(b) —$CH_3$, —$C_2H_5$, or $C_3$ to $C_{25}$ straight-chain, branched or cyclic alkane or alkene comprising one to three heteroatoms selected from the group consisting of O, N and S, and optionally substituted with at least one member selected from the group consisting of Cl, Br, F, I, OH, $NH_2$ and SH;
(c) $C_6$ to $C_{25}$ unsubstituted aryl or unsubstituted heteroaryl having one to three heteroatoms independently selected from the group consisting of O, N and S; and
(d) $C_6$ to $C_{25}$ substituted aryl or substituted heteroaryl having one to three heteroatoms independently selected from the group consisting of O, N and S; and wherein said substituted aryl or substituted heteroaryl has one to three substituents independently selected from the group consisting of:
(1) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH,
(2) OH,
(3) $NH_2$, and
(4) SH;
provided that $A^-$ is not $[CF_3SO_3]^-$, $[HCF_2CF_2SO_3]^-$, $[CF_3HFCCF_2SO_3]^-$, $[HCClFCF_2SO_3]^-$, or $[(CF_3SO_2)_2N]^-$.

DETAILED DESCRIPTION OF THE INVENTION

The present invention relates to novel compositions based on N-substituted pyrrolidinones, said pyrrolidinones having a pendant ammonium cation that is separated from the pyrrolidinone ring by a variable length alkyl spacer. Compositions of the invention should be useful as solvents and, perhaps, as catalysts for many reactions, including aromatic electrophilic substitution, nitration, acylation, esterification, etherification, oligomerization, transesterification, isomerization and hydration. Use of pyrrolidinone-based compositions of the present invention is also advantageous because the pyrrolidinones can be readily prepared from levulinic acid or levulinic acid derivatives obtained from the hydrolysis of inexpensive renewable biomass feedstock.

DEFINITIONS

In this disclosure, a number of terms and abbreviations are used. The following definitions are provided.

By "ionic liquids" is meant organic salts that are fluid around or below 100 degrees C.

By "alkyl" is meant a monovalent radical having the general Formula $C_nH_{2n+1}$. "Monovalent" means having a valence of one.

By "heteroaryl" is meant an aryl group having one or more heteroatoms.

By "hydrocarbyl" is meant a monovalent group containing only carbon and hydrogen.

By "fluoroalkyl" is meant an alkyl group wherein at least one member selected from the hydrogens has been replaced by fluorine. By "perfluoroalkyl" is meant an alkyl group wherein all of the hydrogens have been replaced by fluorines.

By "alkoxy" is meant a straight-chain or branched alkyl group bound via an oxygen atom. By "fluoroalkoxy" is meant an alkoxy group wherein at least one member selected from the hydrogens has been replaced by fluorine. By "perfluoroalkoxy" is meant an alkoxy group wherein all of the hydrogens have been replaced by fluorines.

By "halogen" is meant bromine, iodine, chlorine or fluorine.

By "catalyst" is meant a substance that affects the rate of the reaction but not the reaction equilibrium, and emerges from the process chemically unchanged.

By "homogeneous acid catalyst" is meant a catalyst that is molecularly dispersed with the reactants in the same phase.

By "metal catalyst" is meant a catalyst that is comprised of at least one metal, at least one Raney® metal, compounds thereof or combinations thereof.

By "promoter" is meant an element of the Periodic Table that is added to enhance the physical or chemical function of a catalyst. The promoter can also be added to retard undesirable side reactions and/or affect the rate of a reaction.

By "metal promoter" is meant a metallic compound that is added to enhance the physical or chemical function of a catalyst. The metal promoter can also be added to retard undesirable side reactions and/or affect the rate of a reaction.

"Selectivity" refers to the weight percent of a particular reaction product in the total product weight (including the weight of unreacted reactants).

"Conversion" refers to the weight percent of a particular reactant that is converted to product.

The term "pyrrolidinone" is used synonymously with "pyrrolidone"; the term "pyrrolidine-2-one" is used synonymously with "2-pyrrolidone".

As used herein, the term "biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. According to the invention, biomass may be derived from a single source, or biomass can comprise a mixture derived from more than one source. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

When referring to an alkane, alkene, alkoxy, fluoroalkoxy, perfluoroalkoxy, fluoroalkyl, perfluoroalkyl, aryl or heteroaryl, the term "optionally substituted with at least one member selected from the group consisting of" means that one or more hydrogens on the carbon chain may be independently substituted with one or more of at least one member of the group. For example, substituted $C_2H_5$ may be, without limitations, $CF_2CF_3$, $CH_2CH_2OH$ or $CF_2CF_2I$.

The present invention relates to a composition of matter comprising an ammonium cation and an anion of the Formula:

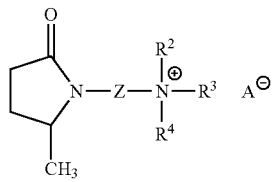

wherein:
(i) Z is $—(CH_2)_n—$, wherein n is an integer from 2 to 12;
(ii) $R^2$, $R^3$ and $R^4$ taken independently are H, $—CH_3$, $—CH_2CH_3$ or $C_3$ to $C_6$ straight-chain or branched monovalent alkyl; and
(iii) $A^-$ is $R^5—SO_3^-$ or $(R^6—SO_2)_2N^-$; wherein $R^5$ and $R^6$ are independently selected from the group consisting of:
 (a) $—CH_3$, $—C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
 (b) $—CH_3$, $—C_2H_5$, or $C_3$ to $C_{25}$ straight-chain, branched or cyclic alkane or alkene comprising one to three heteroatoms selected from the group consisting of O, N and S, and optionally substituted with at least one member selected from the group consisting of Cl, Br, F, I, OH, $NH_2$ and SH;
 (c) $C_6$ to $C_{25}$ unsubstituted aryl or unsubstituted heteroaryl having one to three heteroatoms independently selected from the group consisting of O, N and S; and
 (d) $C_6$ to $C_{25}$ substituted aryl or substituted heteroaryl having one to three heteroatoms independently selected from the group consisting of O, N and S; and wherein said substituted aryl or substituted heteroaryl has one to three substituents independently selected from the group consisting of:
  (1) $—CH_3$, $—C_2H_5$, or $C_3$ to $C_{25}$ straight-chain, branched or cyclic alkane or alkene, optionally substituted with at least one member selected from the group consisting of Cl, Br, F, I, OH, $NH_2$ and SH,
  (2) OH,
  (3) $NH_2$, and
  (4) SH;
  provided that $A^-$ is not $[CF_3SO_3]^-$, $[HCF_2CF_2SO_3]^-$, $[CF_3HFCCF_2SO_3]^-$, $[HCClFCF_2SO_3]^-$, and $[(CF_3SO_2)_2N]^-$.

In a more specific embodiment, n is an integer from 2 to 6.

In an even more specific embodiment, $A^-$ is selected from the group consisting of $[CH_3OSO_3]^-$, $[C_2H_5OSO_3]^-$, $[(CF_3CF_2SO_2)_2N]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, and $[(CF_3CFHCF_2SO_2)_2N]^-$.

Synthesis of N-hydrocarbyl pyrrolidine-2-one

The pyrrolidine-2-one may be synthesized by contacting levulinic acid or an ester thereof with a diamine of the Formula $R^2R^3N$-Z-$NH_2$ in the presence of hydrogen gas and a catalyst according to Reaction (I):

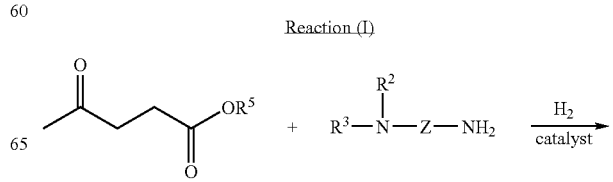

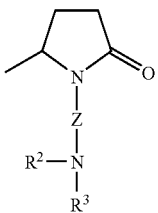

wherein:

(i) Z is —($CH_2$)$_n$—, wherein n is an integer from 2 to 12;
(ii) $R^2$ and $R^3$ taken independently are H, —$CH_3$, —$CH_2CH_3$ or $C_3$ to $C_6$ straight-chain or branched monovalent alkyl; and
(iii) $R^5$ is H, —$CH_3$, —$CH_2CH_3$ or $C_3$ to $C_8$ straight-chain or branched monovalent alkyl.

The pyrrolidine-2-one may also be synthesized by contacting a salt of levulinic acid, such as ammonium levulinate, with a diamine of the Formula $R^2R^3$N-Z-$NH_2$ in the presence of hydrogen gas and a catalyst.

The pyrrolidine-2-one formed in Reaction (I) can be synthesized according to the methods and conditions taught in U.S. Pat. No. 6,818,593 (hereinafter referred to as '593). Although '593 describes the synthesis of 5-methyl-N-alkyl-2-pyrrolidinone from the reductive amination of levulinic acid with nitro compounds, the methods and conditions taught in '593 (column 2, line 66 through column 7, line 21) can be utilized for the process described by Reaction (I) wherein levulinic acid, a salt thereof, or an ester thereof and a diamine are converted to a pyrrolidine-2-one in the presence of hydrogen gas and a catalyst.

Levulinic acid may be obtained from biomass. For the conversion of biomass to levulinic acid, biomass may be contacted with water and an acid catalyst in a train of one or more reactors, preferably under pressure at elevated temperature. This basic process is described, for example, in U.S. Pat. No. 5,608,105, U.S. Pat. No. 5,859,263, U.S. Pat. No. 6,054,611 and U.S. Patent Application 2003/0233011. Generally, cellulose in the biomass is converted to levulinic acid and formate in one or more reactors. Levulinic acid produced from biomass may also be converted to levulinic acid esters for example as described in U.S. 2003/0233011A1 through the reaction of levulinic acid with olefins.

For the synthesis of pyrrolidine-2-ones according to Reaction (I), a molar ratio of diamine to levulinic acid, a salt thereof, or an ester thereof of from about 0.01/1 to about 100/1 is preferred at the start of the reaction; a molar ratio of about 0.3/1 to about 5/1 is further preferred at the start of the reaction. A temperature range of from about 25 degrees C. to about 300 degrees C. is used for the reductive amination reaction; a temperature range of from about 75 degrees C. to about 200 degrees C. is preferred. A pressure range of from about 0.3 MPa to about 20.0 MPa is employed for the reaction; a pressure range of from about 1.3 MPa to about 7.6 MPa is preferred. The reaction may be performed in a non-reacting solvent medium such as water, alcohols, ethers, and pyrrolidones. Alternatively, the excess of diamine can also act as the medium of the reaction.

The principal component of the catalyst useful for Reaction (I) is at least one metal selected from the group consisting of palladium, ruthenium, rhenium, rhodium, iridium, platinum, nickel, cobalt, copper, iron, osmium; compounds thereof; and combinations thereof.

A chemical promoter may augment the activity of a catalyst. The promoter may be incorporated into the catalyst during any step in the chemical processing of the catalyst constituent. The chemical promoter generally enhances the physical or chemical function of the catalyst agent, but can also be added to retard undesirable side reactions. Suitable promoters for the processes used to make the compositions of the invention include metals selected from tin, zinc, copper, gold, silver, and combinations thereof. The preferred metal promoter is tin. Other promoters that can be used are elements selected from Group 1 and Group 2 of the Periodic Table.

The catalyst may be supported or unsupported. A supported catalyst is one in which the active catalyst agent is deposited on a support material by a number of methods, such as spraying, soaking or physical mixing, followed by drying, calcination, and if necessary, activation through methods such as reduction or oxidation. Materials frequently used as a support are porous solids with high total surface areas (external and internal) which can provide high concentrations of active sites per unit weight of catalyst. The catalyst support may enhance the function of the catalyst agent. A supported metal catalyst is a supported catalyst in which the catalyst agent is a metal.

A catalyst that is not supported on a catalyst support material is an unsupported catalyst. An unsupported catalyst may be platinum black or a Raney® (W.R. Grace & Co., Columbia, Md.) catalyst. Raney® catalysts have a high surface area due to selectively leaching an alloy containing the active metal(s) and a leachable metal (usually aluminum). Raney® catalysts have high activity due to high specific area and allow the use of lower temperatures in hydrogenation reactions. The active metals of Raney® catalysts include nickel, copper, cobalt, iron, rhodium, ruthenium, rhenium, osmium, iridium, platinum, palladium; compounds thereof; and combinations thereof.

Promoter metals may also be added to the base Raney® metals to affect selectivity and/or activity of the Raney® catalyst. Promoter metals for Raney® catalysts may be selected from transition metals from Groups IIIA through VIIIA, IB and IIB of the Periodic Table of the Elements. Examples of promoter metals include chromium, molybdenum, platinum, rhodium, ruthenium, osmium, and palladium, typically at about 2% by weight of the total metal.

The catalyst support useful herein can be any solid, inert substance including, but not limited to, oxides such as silica, alumina and titania; barium sulfate; calcium carbonate; and carbons. The catalyst support can be in the form of powder, granules, pellets, or the like.

A preferred support material of the invention is selected from the group consisting of carbon, alumina, silica, silica-alumina, silica-titania, titania, titania-alumina, barium sulfate, calcium carbonate, strontium carbonate, compounds thereof and combinations thereof. Supported metal catalysts can also have supporting materials made from one or more compounds. More preferred supports are carbon, titania and alumina. Further preferred supports are carbons with a surface area greater than 100 $m^2$/g. A further preferred support is carbon with a surface area greater than 200 $m^2$/g. Preferably, the carbon has an ash content that is less than 5% by weight of the catalyst support; the ash content is the inorganic residue (expressed as a percentage of the original weight of the carbon) which remains after incineration of the carbon.

The preferred content of the metal catalyst in the supported catalyst is from about 0.1% to about 20% of the supported catalyst based on metal catalyst weight plus the support weight. A more preferred metal catalyst content range is from about 1% to about 10% of the supported catalyst.

Combinations of metal catalyst and support system may include any one of the metals referred to herein with any of the supports referred to herein. Preferred combinations of metal catalyst and support include palladium on carbon, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina and ruthenium on silica.

Further preferred combinations of metal catalyst and support include palladium on carbon, palladium on alumina, palladium on titania, platinum on carbon, platinum on alumina, rhodium on carbon, rhodium on alumina, ruthenium on carbon and ruthenium on alumina.

Suitable diamines for Reaction (I) may be obtained commercially from, for example, Huntsman (Houston, Tex.) or BASF (Mount Olive, N.J.), or may be synthesized by methods well known to those skilled in the art. For a discussion of the synthesis of diamines, see, for example, Eller, K. and Henkes, E., Diamines and Polyamines (Ullmanns Encyclopedia of Industrial Chemistry (2002) Wiley-VCH Verlag GmbH & Co, Chapter 8) and Experimental Methods in Organic Chemistry, 3$^{rd}$ Edition (Moore, J., Dalrymple, D. and Rodig, O. (eds.) (1982) Saunders College Publishing, NY, Chapter 22). Suitable diamines are those having the Formula $R^2R^3N\text{-}Z\text{-}NH_2$ wherein Z is $-(CH_2)_n-$, wherein n is an integer from 2 to 12 and $R^2$ and $R^3$ taken independently are H, $-CH_3$, $-CH_2CH_3$ or $C_3$ to $C_6$ straight-chain or branched monovalent alkyl.

The formation of pyrrolidine-2-ones may be carried out in batch, sequential batch (i.e., a series of batch reactors) or in continuous mode in any of the equipment customarily employed for continuous process (see for example, H. S. Fogler, Elementary Chemical Reaction Engineering, Prentice-Hall, Inc., N.J., USA).

The pyrrolidinones synthesized according to Reaction (I) may be recovered, for example, by distillation, or by filtration to remove solid acid catalyst particles if present.

Conversion of the Pyrrolidine-2-one to a Quaternary Ammonium Composition of the Invention The non-ring nitrogen of the pyrrolidine-2-one is quaternized to obtain an ammonium salt of the Formula:

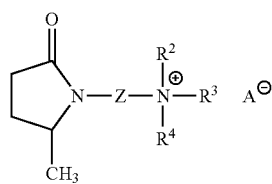

wherein Z is $-(CH_2)_n-$ wherein n is an integer from 2 to 12, $R^2$, $R^3$, and $R^4$ taken independently are $-CH_3$, $-CH_2CH_3$ or $C_3$ to $C_6$ straight-chain or branched monovalent alkyl, and A- is selected from the group consisting of Cl$^-$, Br$^-$, and I$^-$.

In order to form a quaternary ammonium compound, the pyrrolidine-2-one is contacted with an alkylating halide having the Formula $R^1$-A wherein $R^1$ is selected from the group consisting of $-CH_3$, $-CH_2CH_3$ or $C_3$ to $C_6$ straight-chain or branched monovalent alkyl, and A$^-$ is selected from the group consisting of Cl$^-$, Br$^-$, and I$^-$. Methods for performing quaternization reactions are well-known and are described in Organic Chemistry (Morrison and Boyd (ed.) 3$^{rd}$ Edition (1973) Allyn and Bacon, Inc., Boston, Chapter 23.5, pages 752-753).

The quaternization reaction may optionally be carried out in an inert solvent, such as acetonitrile, acetone or dichloromethane. The quaternization may be accomplished by refluxing of the reactants, optionally under an inert atmosphere. When the compositions of the present invention and/or the reactants used for synthesis of the compositions are hygroscopic, it is preferable to carry out the quaternization and/or anion exchange reaction (see below) under conditions that exclude water and air. The alkylating halide is present in slight excess (ca. 5%) at the start of the reaction. The reaction is carried out at a temperature of from about 10 degrees C. to about 80 degrees C.; the reaction is preferably carried out at a temperature of from about 30 degrees C. to about 70 degrees C., more preferably from about 60 degrees C. to about 70 degrees C. The time for the reaction is generally from about 1 minute to about 48 hours; the time for the reaction is preferably from about 30 minutes to about 24 hours.

Anion Exchange

The quaternary ammonium composition may be converted to another composition of the invention by an anion exchange reaction. Thus, the quaternary ammonium compound is contacted with M$^+$A$^-$, wherein M is selected from the group consisting of H, Li, K, Na, Ag, Mg, Ca, Ce, Ba, Rb and Sr, and A$^-$ is an anion as described earlier, to form a composition having the desired anion.

Prior to the exchange reaction, excess alkylating agent may be removed, for example, by evaporation. In addition, the quaternary ammonium compound may be washed with a solvent and dried prior to the anion exchange reaction. The anion exchange reaction may be carried out by mixing the quaternary ammonium compound with M$^+$A$^-$, optionally under an inert atmosphere. The anion exchange reaction may be carried out at a temperature of from about −20 degrees C. to about 100 degrees C. for a time of about 1 second to about 72 hours. Solvents useful in the reaction should be inert to the reactants and products, and include methanol, ethanol, acetone and acetonitrile. Choice of the appropriate solvent or mixture of solvents will allow for separation of the composition comprising the desired anion from the composition comprising the less desired anion as is well known in the art. Additional techniques may be utilized to enhance the anion exchange reaction, such as ultrasonication as taught in WO 03/048078.

The composition comprising the desired anion can be recovered by a suitable technique such as evaporation of the reaction solvent under reduced pressure, decantation and/or filtration to remove precipitated salts.

Compositions (ionic liquids) of the present invention can be utilized in one phase systems or multiple phase systems as solvents or, perhaps, as catalysts. The physical and chemical properties of the compositions of the present invention can be specifically selected by choice of the appropriate cation and anion. For example, increasing the chain length of one or more alkyl chains of the cation will affect properties such as the melting point, hydrophilicity/lipophilicity, density and solvation strength of the ionic liquid. Choice of the anion can affect, for example, the melting point, the water solubility and the acidity and coordination properties of the composition. Thus it may be desirable to perform an anion exchange reaction by contacting the composition with M$^+$A$^-$ as described above to replace a less desirable anion of an ionic liquid with an anion that gives the desired chemical and physical properties for the ionic liquid composition. Effects of cation and anion on the physical and chemical properties of ionic liquids are known to those skilled in the art and are reviewed in detail by Wassersheid and Keim (Angew. Chem. Int. Ed, supra) and Sheldon (Chem. Commun., supra).

Preparation of Polytrimethylene Ether Glycol

Compositions of the present invention are useful for the polymerization of 1,3-propanediol. To prepare polytrimethylene ether glycol, 1,3-propanediol is contacted with at least one polycondensation catalyst and at least one ionic liquid of the invention to form a polyether phase comprising polytrimethylene ether glycol and an ionic liquid phase. The polyether phase is then separated from the ionic liquid phase.

The 1,3-propanediol may be obtained commercially or by any of the various chemical routes or by biochemical transformation routes well known to those skilled in the art.

The temperature of the process is preferably controlled to achieve high yields of desired molecular weight and a minimum of color formation. The polycondensation reaction is preferably carried out at a temperature of from about 120 degrees C. to about 250 degrees C. In one embodiment, the temperature is from about 120 degrees C. to about 210 degrees C.; in another embodiment the temperature is from about 120 degrees C. to about 180 degrees C.; in still another embodiment, the temperature is from about 140 degrees C. to about 180 degrees C.

The polycondensation may be carried out under an inert atmosphere, such as nitrogen or argon. In another embodiment, the polycondensation is carried out at a pressure of less than about 100 KPa; in additional embodiments the reaction is carried out at a pressure of less than about 67 KPa or less than about 33 KPa.

The time for the reaction will depend on many factors, such as the reactants, reaction conditions and reactor. One skilled in the art will know to adjust the time for the reaction to achieve high yields of polytrimethylene ether glycol (or copolymers thereof) of the desired molecular weight.

The at least one polycondensation catalyst is a homogeneous acid catalyst. Suitable homogeneous acid catalysts are those having a pKa of less than about 4; in another embodiment, suitable homogeneous acid catalysts are those having a pKa of less than about 2.

Suitable polycondensation catalysts include inorganic acids, organic sulfonic acids, heteropolyacids, fluoroalkyl sulfonic acids, metal sulfonates, metal trifluoroacetates, compounds thereof and combinations thereof. In yet another embodiment, the at least one polycondensation catalyst is a homogeneous acid catalyst selected from the group consisting of sulfuric acid, fluorosulfonic acid, phosphorous acid, p-toluenesulfonic acid, benzenesulfonic acid, phosphotungstic acid, phosphomolybdic acid, trifluoromethanesulfonic acid, nonafluorobutanesulfonic acid, 1,1,2,2-tetrafluoroethanesulfonic acid, 1,1,2,3,3,3-hexafluoropropanesulfonic acid, bismuth triflate, yttrium triflate, ytterbium triflate, neodymium triflate, lanthanum triflate, scandium triflate, and zirconium triflate. The catalyst is used at a concentration of from about 0.1% to about 20% by weight of the 1,3-propanediol reactant.

The polycondensation reaction may be carried out as a batch or continuous process. Reactor configurations, as well as a continuous process for polycondensation of 1,3-propanediol reactant, are described in U.S. Pat. No. 6,720,459, Column 5, line 49 through Column 9, line 26, and FIGS. 1 through 6.

An advantage to the use of at least one ionic liquid in this reaction is that the reaction product comprises a polyether phase comprising polytrimethylene ether glycol and an ionic liquid phase that comprises the acid catalyst. Thus the polytrimethylene ether glycol product or products in the polyether phase is/are easily recoverable from the acid catalyst by, for example, decantation. In a preferred embodiment, the acid catalyst and the at least one ionic liquid are recycled and used in subsequent reactions.

GENERAL MATERIALS AND METHODS

The following abbreviations are used:

Nuclear magnetic resonance is abbreviated NMR; gas chromatography is abbreviated GC; gas chromatography-mass spectrometry is abbreviated GC-MS; thin layer chromatography is abbreviated TLC; thermogravimetric analysis (using a Universal V3.9A TA instrument analyser (TA Instruments, Inc., Newcastle, Del.)) is abbreviated TGA. Centigrade is abbreviated C, mega Pascal is abbreviated MPa, gram is abbreviated g, kilogram is abbreviated Kg, milliliter(s) is abbreviated ml(s), hour is abbreviated hr; weight percent is abbreviated wt %; milliequivalents is abbreviated meq; melting point is abbreviated Mp; differential scanning calorimetry is abbreviated DSC.

Tetrahydrofuran, iodopropane, acetonitrile, iodoperfluorohexane, toluene, 1,3-propanediol, oleum (20% $SO_3$), sodium sulfite ($Na_2SO_3$, 98%), and acetone were obtained from Acros (Hampton, N.H.). Potassium metabisulfite ($K_2S_2O_5$, 99%), was obtained from Mallinckrodt Laboratory Chemicals (Phillipsburg, N.J.). Potassium sulfite hydrate ($KHSO_3 \cdot xH_2O$, 95%), sodium bisulfite ($NaHSO_3$), sodium carbonate, magnesium sulfate, ethyl ether, trioctyl phosphine, phosphotungstic acid and 1-ethyl-3-methylimidazolium chloride (98%) were obtained from Aldrich (St. Louis, Mo.). Sulfuric acid and methylene chloride were obtained from EMD Chemicals, Inc. (Gibbstown, N.J.). Perfluoro(ethylvinyl ether), perfluoro(methylvinyl ether), hexafluoropropene and tetrafluoroethylene were obtained from DuPont Fluoroproducts (Wilmington, Del.). 1,1,2,2-Tetrafluoro-2-(pentafluoroethoxy)sulfonate was obtained from SynQuest Laboratories, Inc. (Alachua, Fla.). ESCAT-142 (Pd/C catalyst) was obtained from Engelhard Corp. (Iselin, N.J.). Ethyl levulinate and N,N-dimethylethylenediamine were obtained from Alfa Aesar (Ward Hill, Mass.). Acetonitrile, iodopropane, bromopropane, bromopentane, ethanol, sodium hydroxide, triflic acid, potassium triflate, 1-dodecene, p-xylene, bis-trifluoromethanesulfonimide, and bis-hexafluorophosphate were obtained from Sigma-Aldrich (St. Louis, Mo.).

Preparation of Anions Not Generally Available Commercially (A) Synthesis of Potassium 1,1,2,2-tetrafluoroethanesulfonate (TFES-K) ($[HCF_2CF_2SO_3]^-$)

A 1-gallon Hastelloy® C276 reaction vessel was charged with a solution of potassium sulfite hydrate (176 g, 1.0 mol), potassium metabisulfite (610 g, 2.8 mol) and deionized water (2000 ml). The pH of this solution was 5.8. The vessel was cooled to 18 degrees C., evacuated to 0.10 MPa, and purged with nitrogen. The evacuate/purge cycle was repeated two more times. To the vessel was then added tetrafluoroethylene (TFE, 66 g), and it was heated to 100 degrees C. at which time the inside pressure was 1.14 MPa. The reaction temperature was increased to 125 degrees C. and kept there for 3 hr. As the TFE pressure decreased due to the reaction, more TFE was added in small aliquots (20-30 g each) to maintain operating pressure roughly between 1.14 and 1.48 MPa. Once 500 g (5.0 mol) of TFE had been fed after the initial 66 g precharge, the vessel was vented and cooled to 25 degrees C. The pH of the clear light yellow reaction solution was 10-11. This solution was buffered to pH 7 through the addition of potassium metabisulfite (16 g).

The water was removed in vacuo on a rotary evaporator to produce a wet solid. The solid was then placed in a freeze dryer (Virtis Freezemobile 35xl; Gardiner, N.Y.) for 72 hr to reduce the water content to approximately 1.5 wt % (1387 g crude material). The theoretical mass of total solids was 1351 g. The mass balance was very close to ideal and the isolated solid had slightly higher mass due to moisture. This added freeze drying step had the advantage of producing a free-flowing white powder whereas treatment in a vacuum oven resulted in a soapy solid cake that was very difficult to remove and had to be chipped and broken out of the flask.

The crude TFES-K can be further purified and isolated by extraction with reagent grade acetone, filtration, and drying.

$^{19}$F NMR (D$_2$O) δ −122.0.(dt, J$_{FH}$=6 Hz, J$_{FF}$=6 Hz, 2F); −136.1 (dt, J$_{FH}$=53 Hz, 2F).

$^1$H NMR (D$_2$O) δ 6.4 (tt, J$_{FH}$=53 Hz, J$_{FH}$=6 Hz, 1 H).

% Water by Karl-Fisher titration: 580 ppm.

Analytical calculation for C$_2$HO$_3$F$_4$SK: C, 10.9: H, 0.5: N, 0.0

Experimental results: C, 11.1: H, 0.7: N, 0.2.

Mp (DSC): 242 degrees C.

TGA (air): 10% wt. loss @ 367 degrees C., 50% wt. loss @ 375 degrees C.

TGA (N$_2$): 10% wt. loss @ 363 degrees C., 50% wt. loss @ 375 degrees C.

(B) Synthesis of potassium-1,1,2-trifluoro-2-(perfluoroethoxy)ethanesulfonate (TPES-K) ([CF$_3$CF$_2$OCFHCF$_2$SO$_3$]$^-$)

A 1-gallon Hastelloy® C276 reaction vessel was charged with a solution of potassium sulfite hydrate (88 g, 0.56 mol), potassium metabisulfite (340 g, 1.53 mol) and deionized water (2000 ml). The vessel was cooled to 7 degrees C., evacuated to 0.05 MPa, and purged with nitrogen. The evacuate/purge cycle was repeated two more times. To the vessel was then added perfluoro(ethylvinyl ether) (PEVE, 600 g, 2.78 mol), and it was heated to 125 degrees C. at which time the inside pressure was 2.31 MPa. The reaction temperature was maintained at 125 degrees C. for 10 hr. The pressure dropped to 0.26 MPa at which point the vessel was vented and cooled to 25 degrees C. The crude reaction product was a white crystalline precipitate with a colorless aqueous layer (pH=7) above it.

The $^{19}$F NMR spectrum of the white solid showed pure desired product, while the spectrum of the aqueous layer showed a small but detectable amount of a fluorinated impurity. The desired isomer is less soluble in water so it precipitated in isomerically pure form.

The product slurry was suction filtered through a fritted glass funnel, and the wet cake was dried in a vacuum oven (60 degrees C., 0.01 MPa) for 48 hr. The product was obtained as off-white crystals (904 g, 97% yield).

$^{19}$F NMR (D$_2$O) δ −86.5.(s, 3F); −89.2, −91.3 (subsplit ABq, J$_{FF}$=147 Hz, 2F);

−119.3, −121.2 (subsplit ABq, J$_{FF}$=258 Hz, 2F); −144.3 (dm, J$_{FH}$=53 Hz, 1F).

$^1$H NMR (D$_2$O) δ 6.7 (dm, J$_{FH}$=53 Hz, 1H).

Mp (DSC) 263 degrees C.

Analytical calculation for C$_4$HO$_4$F$_8$SK: C, 14.3: H, 0.3 Experimental results: C, 14.1: H, 0.3.

TGA (air): 10% wt. loss @ 359 degrees C., 50% wt. loss @ 367 degrees C.

TGA (N$_2$): 10% wt. loss @ 362 degrees C., 50% wt. loss @ 374 degrees C.

(C) Synthesis of potassium-1,1,2-trifluoro-2-(trifluoromethoxy)ethanesulfonate (TTES-K) ([CF$_3$OCFHCF$_2$SO$_3$]$^-$)

A 1-gallon Hastelloy® C276 reaction vessel was charged with a solution of potassium sulfite hydrate (114 g, 0.72 mol), potassium metabisulfite (440 g, 1.98 mol) and deionized water (2000 ml). The pH of this solution was 5.8. The vessel was cooled to −35 degrees C., evacuated to 0.08 MPa, and purged with nitrogen. The evacuate/purge cycle was repeated two more times. To the vessel was then added perfluoro(methylvinyl ether) (PMVE, 600 g, 3.61 mol) and it was heated to 125 degrees C. at which time the inside pressure was 3.29 MPa. The reaction temperature was maintained at 125 degrees C. for 6 hr. The pressure dropped to 0.27 MPa at which point the vessel was vented and cooled to 25 degrees C. Once cooled, a white crystalline precipitate of the desired product formed leaving a colorless clear aqueous solution above it (pH=7).

The $^{19}$F NMR spectrum of the white solid showed pure desired product, while the spectrum of the aqueous layer showed a small but detectable amount of a fluorinated impurity.

The solution was suction filtered through a fritted glass funnel for 6 hr to remove most of the water. The wet cake was then dried in a vacuum oven at 0.01 MPa and 50 degrees C. for 48 hr. This gave 854 g (83% yield) of a white powder. The final product was isomerically pure (by $^{19}$F and $^1$H NMR) since the undesired isomer remained in the water during filtration.

$^{19}$F NMR (D$_2$O) δ −59.9.(d, J$_{FH}$=4 Hz, 3F); −119.6, −120.2 (subsplit ABq, J=260 Hz, 2F); −144.9 (dm, J$_{FH}$=53 Hz, 1F).

$^1$H NMR (D$_2$O) δ 6.6 (dm, J$_{FH}$=53 Hz, 1H).

% Water by Karl-Fisher titration: 71 ppm.

Analytical calculation for C$_3$HF$_6$SO$_4$K: C, 12.6: H, 0.4: N, 0.0

Experimental results: C, 12.6: H, 0.0: N, 0.1.

Mp (DSC) 257 degrees C.

TGA (air): 10% wt. loss @ 343 degrees C., 50% wt. loss @ 358 degrees C.

TGA (N$_2$): 10% wt. loss @ 341 degrees C., 50% wt. loss @ 357 degrees C.

(D) Synthesis of Sodium 1,1,2,3,3,3-hexafluoropropanesulfonate (HFPS-Na) ([CF$_3$HFCCF$_2$SO$_3$]$^-$)

A 1-gallon Hastelloy® C reaction vessel was charged with a solution of anhydrous sodium sulfite (25 g, 0.20 mol), sodium bisulfite 73 g, (0.70 mol) and of deionized water (400 ml). The pH of this solution was 5.7. The vessel was cooled to 4 degrees C., evacuated to 0.08 MPa, and then charged with hexafluoropropene (HFP, 120 g, 0.8 mol, 0.43 MPa). The vessel was heated with agitation to 120 degrees C. and kept there for 3 hr.

The pressure rose to a maximum of 1.83 MPa and then dropped down to 0.27 MPa within 30 minutes. At the end, the vessel was cooled and the remaining HFP was vented, and the reactor was purged with nitrogen. The final solution had a pH of 7.3.

The water was removed in vacuo on a rotary evaporator to produce a wet solid. The solid was then placed in a vacuum oven (0.02 MPa, 140 degrees C., 48 hr) to produce 219 g of white solid which contained approximately 1 wt % water. The theoretical mass of total solids was 217 g.

The crude HFPS-Na can be further purified and isolated by extraction with reagent grade acetone, filtration, and drying.

$^{19}$F NMR (D$_2$O) δ −74.5 (m, 3F); −113.1, −120.4 (ABq, J=264 Hz, 2F); −211.6 (dm, 1F).

$^1$H NMR (D$_2$O) δ 5.8 (dm, J$_{FH}$=43 Hz, 1H).

Mp (DSC) 126 degrees C.

TGA (air): 10% wt. loss @ 326 degrees C., 50% wt. loss @ 446 degrees C.

TGA (N$_2$): 10% wt. loss @ 322 degrees C., 50% wt. loss @ 449 degrees C.

Example 1

Synthesis of 1-(2-N,N,N-dimethylpropylaminoethyl)-5-methyl pyrrolidine-2-one 1,1,2-trifluoro-2-(perfluoroethoxy)ethanesulfonate, an Ionic Liquid of the Present Invention Ethyl levulinate (18.5 g), N,N-dimethylethylenediamine (11.3 g), and 5% Pd/C (ESCAT-142, 1.0 g) were mixed in a 400 ml shaker tube reactor. The reaction was carried out at 150 degrees C. for 8 hr under 6.9 MPa of H$_2$. The reactants and products were analyzed by gas chromatography on a HP-6890 GC (Agilent Technologies; Palo Alto, Calif.) and HP-5972A GC-MS detector equipped with a 25 M×0.25 MM ID CP-Wax 58 (FFAP) column. The GC yields were obtained by adding methoxyethyl ether as the internal standard. The ethyl levulinate conversion was 99.7%, and the product selectivity for 1-(2-N,N-dimethylaminoethyl)-5-methyl-pyrrolidine-2-one was 96%.

For the quaternization reaction, purified 1-(2-N,N-dimethylaminoethyl)-5-methyl-pyrrolidine-2-one (1.7 g) was placed in 5 g of dry acetonitrile, and 1.69 g of 1-iodopropane was added. This mixture was refluxed overnight under a nitrogen atmosphere; the reaction was shown to be complete via TLC, yielding the iodide salt of the quaternary ammonium compound. The acetonitrile was then removed under vacuum.

The ionic liquid 1-(2-N,N,N-dimethylpropylaminoethyl)-5-methyl pyrrolidine-2-one 1,1,2-trifluoro-2-(perfluoroethoxy)ethanesulfonate is prepared by reacting 1-(2-N,N,N-dimethylpropylaminoethyl)-5-methyl pyrrolidine-2-one with 1,1,2-trifluoro-2-(perfluoroethoxy)ethanesulfonate. 1-(2-N,N,N-Dimethylpropylaminoethyl)-5-methyl-pyrrolidine-2-one iodide (3 g) is added to 20 m/s of acetone, and an equimolar amount of potassium 1,1,2-trifluoro-2-(perfluoroethoxy)ethanesulfonate is added. The mixture is heated for 17 hours at 60 degrees C.; the solvent is removed by heating, and the solid potassium iodide is removed by filtration, yielding the ionic liquid.

Examples 2-4 Exemplify the Polymerization of Propanediol

Example 2

Polymerization of Propanediol Using the Ionic Liquid of Example 1

1,3-Propanediol (20 g) is placed in a three neck round bottomed flask. To this is added tetraethaneperfluorosulfonic acid (0.8 wt % in the final solution). The ionic liquid 1-(2-N,N,N-dimethylpentylaminoethyl)-5-methyl-pyrrolidine-2-one 1,1,2-trifluoro-2-(perfluoroethoxy)ethanesulfonate (4 g) is added, and the solution and contents are purged with nitrogen for two hours. The homogeneous solution is heated using an oil bath at 160 degrees C. under a nitrogen atmosphere. Water is slowly evolved and collected in a condenser. After approximately 9-10 hours the solution goes from a single phase to a two-phase system. Upon cooling to 75 degrees C., two phases result. The top phase is shown via NMR to be essentially polymerized propanediol (polyol). The molecular weight (Mn) is about 3000 after 10 hours. The acid and ionic liquid are found to be essentially in the lower phase with polyol in the upper phase. The lower phase can easily be separated and recycled.

Example 3

Polymerization of Propanediol with Recycling of the Ionic Liquid 1,3-Propanediol (30 g) is placed in a three neck round bottomed flask. To this is added 1,1,2,3,3,3-hexafluoropropanesulfonic acid (0.15 g; 0.5 wt % in the final solution). The ionic liquid 1-(2-N,N,N-dimethylpentylaminoethyl)-5-methyl-pyrrolidine-2-one 1,1,2-trifluoro-2-(perfluoroethoxy)ethanesulfonate (2 g) is also added, and the solution and contents are purged with nitrogen for two hours. The homogeneous solution is heated using an oil bath at 160 degrees C. under a nitrogen atmosphere. Water is slowly evolved and collected in a condenser. After approximately 26 hours the solution goes from a single phase to a two-phase system. Upon cooling to 75 degrees C., two phases are clearly visible. The top phase is shown via NMR to be essentially polymerized propanediol (polyol). The molecular weight (Mn) is approximately 2613, as determined using NMR. The total unsaturated ends is 30 meq/Kg. The acid and ionic liquid are found to be essentially in the lower phase with polyol in the upper phase.

A portion of the lower phase (2 g) is removed using a glass pipette. This is placed in a three neck round bottomed flask, followed by 28 g of 1,3-propanediol. The homogeneous solution is heated using an oil bath at 160 degrees C. under a nitrogen atmosphere. Water is slowly evolved and collected in a condenser. After approximately 30 hours the solution goes from a single phase to a two-phase system. Upon cooling to 75 degrees C., two phases are clearly visible. The top phase is shown by NMR to be essentially polymerized propanediol (polyol). The molecular weight (Mn) is approximately 3108 by NMR. The total unsaturated ends is 50 meq/Kg.

Example 4

Polymerization of Propanediol 1,3-Propanediol is placed in a three neck round bottomed flask. To this Is added 0.3 g of phosphotungstic acid and 2 g of the ionic liquid 1-(2-N,N-dimethylpentylaminoethyl)-5-methyl-pyrrolidine-2-one 1,1,2-trifluoro-2-(perfluoroethoxy)ethanesulfonate, and the solution and contents are purged with nitrogen for two hours. The homogeneous solution is heated using an oil bath at 160 degrees C. under a nitrogen atmosphere. Water is slowly evolved and collected in a condenser. After approximately 24 hours the solution goes from a single phase to a two-phase system. Upon cooling to 75 degrees C., two phases are clearly visible. The top phase is shown by NMR to be essentially polymerized propanediol (polyol). The molecular weight (Mn) is approximately 4319 by NMR. The total unsaturated ends is 81 meq/Kg.

What is claimed is:

1. A composition of matter comprising an ammonium cation and anion of the Formula:

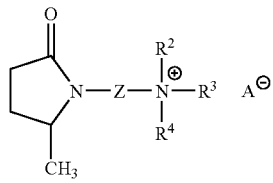

wherein:
(i) Z is —$(CH_2)_n$—, wherein n is an integer from 2 to 12;
(ii) $R^2$, $R^3$ and $R^4$ taken independently are H, —$CH_3$, —$CH_2CH_3$ or $C_3$ to $C_6$ straight-chain or branched monovalent alkyl; and
(iii) $A^-$ is $R^5$—$SO_3^-$ or $(R^6$—$SO_2)_2N$; wherein $R^5$ and $R^6$ are independently selected from the group consisting of:
(a) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(b) —$CH_3$, —$C_2H_5$, or $C_3$ to $C_{25}$ straight-chain, branched or cyclic alkane or alkene comprising one to three heteroatoms selected from the group consisting of O, N and S, and optionally substituted with at least one member selected from the group consisting of Cl, Br, F, I, OH, $NH_2$ and SH;
(c) $C_6$ to $C_{25}$ unsubstituted aryl or unsubstituted heteroaryl having one to three heteroatoms independently selected from the group consisting of O, N and S; and
(d) $C_6$ to $C_{25}$ substituted aryl or substituted heteroaryl having one to three heteroatoms independently selected from the group consisting of O, N and S; and wherein said substituted aryl or substituted heteroaryl has one to three substituents independently selected from the group consisting of:
(1) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH,
(2) OH,
(3) $NH_2$, and
(4) SH;
provided that $A^-$ is not $[CF_3SO_3]^-$, $[HCF_2CF_2SO_3]^-$, $[CF_3HFCCF_2SO_3]^-$, $[HCClFCF_2SO_3]^-$, or $[(CF_3SO_2)_2N]^-$.

2. The composition of claim 1 wherein $A^-$ is selected from the group consisting of $[CH_3OSO_3]^-$, $[C_2H_5OSO_3]^-$, $[(CF_3CF_2SO_2)_2N]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, and $[(CF_3CFHCF_2SO_2)_2N]^-$.

3. The composition of claim 1 wherein Z is —$(CH_2)_n$—, wherein n is an integer from 2 to 6.

4. The composition of claim 3 wherein $A^-$ is selected from the group consisting of $[CH_3OSO_3]^-$, $[C_2H_5OSO_3]^-$, $[(CF_3CF_2SO_2)_2N]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, and $[(CF_3CFHCF_2SO_2)_2N]^-$.

* * * * *

UNITED STATES PATENT AND TRADEMARK OFFICE
CERTIFICATE OF CORRECTION

PATENT NO. : 7,625,941 B2 Page 1 of 1
APPLICATION NO. : 11/525751
DATED : December 1, 2009
INVENTOR(S) : Harmer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 488 days.

Signed and Sealed this

Second Day of November, 2010

David J. Kappos
*Director of the United States Patent and Trademark Office*